US007641796B2

(12) United States Patent
Stroot et al.

(10) Patent No.: US 7,641,796 B2

(45) Date of Patent: Jan. 5, 2010

(54) ANAEROBIC DIGESTION PROCESS FOR LOW-SOLID WASTE

(75) Inventors: Peter George Stroot, Lutz, FL (US); Matthew Raymond Cutter, Tampa, FL (US)

(73) Assignee: University of South Florida, Tampa, FL (US)

(*) Notice: Subject to any disclaimer, the term of this patent is extended or adjusted under 35 U.S.C. 154(b) by 216 days.

(21) Appl. No.: 11/420,335

(22) Filed: May 25, 2006

(65) Prior Publication Data

US 2006/0266703 A1 Nov. 30, 2006

Related U.S. Application Data

(60) Provisional application No. 60/594,991, filed on May 25, 2005.

(51) Int. Cl.

*C02F 11/04* (2006.01)

*C02F 3/30* (2006.01)

(52) U.S. Cl. ....................... 210/603; 210/609; 210/613; 210/630

(58) Field of Classification Search ................. 210/603, 210/605, 609, 612, 613, 620, 630

See application file for complete search history.

(56) References Cited

U.S. PATENT DOCUMENTS

| | | | | | |
|---|---|---|---|---|---|
| 2,064,529 | A | * | 12/1936 | Fischer et al. | 210/603 |
| 2,850,449 | A | * | 9/1958 | Torpey | 210/609 |
| 3,220,945 | A | * | 11/1965 | Torpey | 210/609 |
| 3,386,910 | A | * | 6/1968 | Forrest | 210/624 |
| RE26,514 | E | * | 12/1968 | Albertson et al. | 110/342 |
| 3,440,165 | A | * | 4/1969 | Davis et al. | 210/609 |
| 3,787,316 | A | * | 1/1974 | Brink et al. | 210/608 |
| 4,213,857 | A | | 7/1980 | Ishida et al. | |
| 4,277,342 | A | * | 7/1981 | Hayes et al. | 435/262.5 |
| 4,289,625 | A | | 9/1981 | Tarman et al. | |
| 4,315,823 | A | * | 2/1982 | Witt et al. | 210/605 |
| 4,551,243 | A | * | 11/1985 | Martin | 210/180 |
| 4,735,724 | A | | 4/1988 | Chynoweth et al. | |
| 4,975,195 | A | * | 12/1990 | Urbani | 210/608 |
| 4,988,442 | A | | 1/1991 | Highsmith et al. | |

(Continued)

FOREIGN PATENT DOCUMENTS

| | | | |
|---|---|---|---|
| JP | 59-388 | * | 1/1984 |

*Primary Examiner*—Fred Prince

(74) *Attorney, Agent, or Firm*—Michele L. Lawson; Smith & Hopen, P.A.

(57) ABSTRACT

An anaerobic digestion process for the treatment of domestic wastewater sludge that requires less space and funding to construct. Sludge to be treated is combined with recycled anaerobic digester sludge to form a blended sludge. The recycled anaerobic digester sludge provides a source of microorganisms necessary to initiate the breakdown of organic matter in the sludge to be treated. The sludge is then concentrated to increase total solids content to about 10-20%. Excess liquid is removed from the concentrated sludge. The concentrated sludge is then digested in an anaerobic reactor system such as a plug-flow reactor. Some benefits of the system's reduced volume, as a result of concentration of the sludge, include elimination of the necessity of substantially continuous stirring and the new possibilities for the types of construction to be used for the reactor. In addition to the reduced cost of the process itself, the process creates biogas that can be used to offset energy requirements for the process.

20 Claims, 2 Drawing Sheets

U.S. PATENT DOCUMENTS 5,076,927 A 12/1991 Hunter
H1149 H 3/1993 Wyman et al.
5,207,911 A 5/1993 Pellegrin et al.
5,264,349 A 11/1993 De Baere
5,338,445 A 8/1994 Zumbragel et al.
5,451,319 A 9/1995 Kobayashi
5,723,048 A 3/1998 Kobayashi et al.
5,733,758 A * 3/1998 Nguyen ...................... 435/162
6,077,430 A * 6/2000 Chudoba et al. ............ 210/605
6,254,775 B1 7/2001 McElvaney
6,299,774 B1 * 10/2001 Ainsworth et al. .......... 210/603
6,444,124 B1 9/2002 Onyeche et al.
6,692,642 B2 2/2004 Josse et al.
2004/0144735 A1 * 7/2004 Shepherd et al. ............ 210/769

* cited by examiner

*2-Stage Anaerobic Digester (Conventional)*

(Prior Art)

*High-rate Anaerobic Digester*

(Prior Art)

ANAEROBIC DIGESTION PROCESS FOR LOW-SOLID WASTE

CROSS REFERENCE TO RELATED APPLICATIONS

This application claims priority to U.S. Provisional Patent Application 60/594,991, entitled, "Anaerobic Digestion Process for Low-Solid Wastes", filed May 25, 2005, the contents of which are herein incorporated by reference.

FIELD OF INVENTION

This invention relates to wastewater treatment. More particularly, this invention relates to an anaerobic digestion process for the treatment of domestic wastewater sludge utilizing thickened sludge allowing for reduced reactor size.

BACKGROUND OF THE INVENTION

There is considerable interest in the treatment of wastewater sludge. Anaerobic digestion of municipal wastewater sludge typically requires the use of large holding tanks sized to accommodate enough sludge to account for a 20-day hydraulic retention time. In addition to these tanks, equipment is used to constantly stir the contents. This new process requires a much smaller tank and no stirring equipment, and yet does not sacrifice performance as compared to standard anaerobic digestion processes. Resulting equipment costs and capital costs are reduced considerably. Land requirements are similarly reduced.

Anaerobic digestion is a microbiological process in which organic materials are broken down by the action of microorganisms in the absence of oxygen. The anaerobic microorganisms reduce the quantity of organic matter present in the biologically activated sludge thereby generating bio-gas having a relatively high methane gas content. The stabilized sludge is typically removed from a digestion tank for dewatering and disposal. The methane gas can be burned off or recovered to supply energy to heat the digesters as well as supply energy for use elsewhere in the treatment facility. There exists a great need to maximize the effectiveness and costs of the anaerobic digestion to allow municipalities and other treatment facilities to operate efficiently and reduce the burdens on space. This invention serves these important needs and others as will become apparent.

SUMMARY OF INVENTION

An anaerobic digestion process for the treatment of domestic wastewater sludge that requires less space and funding to construct. Sludge to be treated is combined with recycled anaerobic digester sludge to form a blended sludge. The recycled anaerobic digester sludge provides a source of microorganisms necessary to initiate the breakdown of organic matter in the sludge to be treated. The sludge is then concentrated to increase total solids content to about 10-20%. Excess liquid is removed from the concentrated sludge. The concentrated sludge is then digested in an anaerobic reactor system such as a plug-flow reactor. Some benefits of the system's reduced volume, as a result of concentration of the sludge, include elimination of the necessity of substantially continuous stirring and the new possibilities for the types of construction to be used for the reactor. In addition to the reduced cost of the process itself, the process creates biogas that can be used to offset energy requirements for the process.

In accordance with one aspect of the invention there is provided a method for the treatment of sludge generated in a wastewater treatment system including the steps of blending sludge to be treated with recycled anaerobic digester sludge to form a blended sludge, concentrating the blended sludge wherein the total solids content is increased to about 10% to about 20% and excess liquid is removed, transferring the excess liquid for aerobic digestion, digesting the concentrated sludge in an anaerobic digestion systems and recycling a portion of the digester waste stream to provide as recycled anaerobic digester sludge input for the blending step. In certain embodiments the sludge to be treated is primary and waste activated sludge. In an advantageous embodiment the reactor of the anaerobic digestion system is a plug-flow reactor. In a further embodiments the temperature of the anaerobic digestion system is maintained by a heating jacket. The anaerobic digestion system may also be insulated to maintain a substantially constant temperature. In certain embodiments the reactor of the anaerobic digestion system is small volume reactor relative to the size of a reactor used in a conventional digestion process. Reducing reactor size results in a significant economic advantage and allows the use of standard-size plastic or metal tanks as opposed to the pre-stressed concrete required in larger systems. In certain aspects the digesting of the concentrated sludge in an anaerobic digestion system is performed in the absence of substantially continuous stirring. Eliminating the requirement for stirring substantially reduces the cost and complexity of the system. In certain aspects the blended sludge is concentrated using a centrifuge. In alternative aspects the blended sludge is concentrated using a belt filter press. Alternatively a combination of these means, and other, could be used to concentrate the blended sludge. The concentrated, blended sludge can be transferred to the anaerobic digestion system using an auger. In an advantageous embodiment a portion of the produced biogas can be captured to offset the cost of the wastewater treatment process.

In alternative aspects the present invention provides a method for treating sludge generated in a wastewater treatment system including the steps of blending sludge to be treated with recycled anaerobic digester sludge to form a blended sludge, concentrating the blended sludge wherein the total solids content is increased to about 10% to about 20% and excess liquid is removed, transferring the excess liquid for aerobic digestion, digesting the concentrated sludge in a plug-flow reactor anaerobic digestion system; and recycling a portion of the digester waste stream to provide as recycled anaerobic digester sludge input for the blending step. In certain embodiments the anaerobic digestion system is maintained a substantially constant temperature. The temperature of the anaerobic digestion system can be maintained by a heating jacket. The anaerobic digestion system may also be insulated to maintain a substantially constant temperature. In certain aspects the digesting of the concentrated sludge in an anaerobic digestion system is performed in the absence of substantially continuous stirring.

In further alternative aspects the present invention provides a method for treating sludge generated in a wastewater treatment system comprising the steps of providing primary and waste-activated sludge to be treated, concentrating the sludge wherein the total solids content is increased to about 10% to about 20% and excess liquid is removed, transferring the excess liquid for aerobic digestion and digesting the concentrated sludge in a plug-flow reactor anaerobic digestion system. In certain embodiments the anaerobic digestion system is maintained a substantially constant temperature. The temperature of the anaerobic digestion system can be maintained by a heating jacket. The anaerobic digestion system may also be insulated to maintain a substantially constant temperature. In certain aspects the digesting of the concentrated sludge in an anaerobic digestion system is performed in the absence of substantially continuous stirring.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The disclosed invention is an anaerobic digestion process for the treatment of domestic wastewater sludge.

Figure 1:
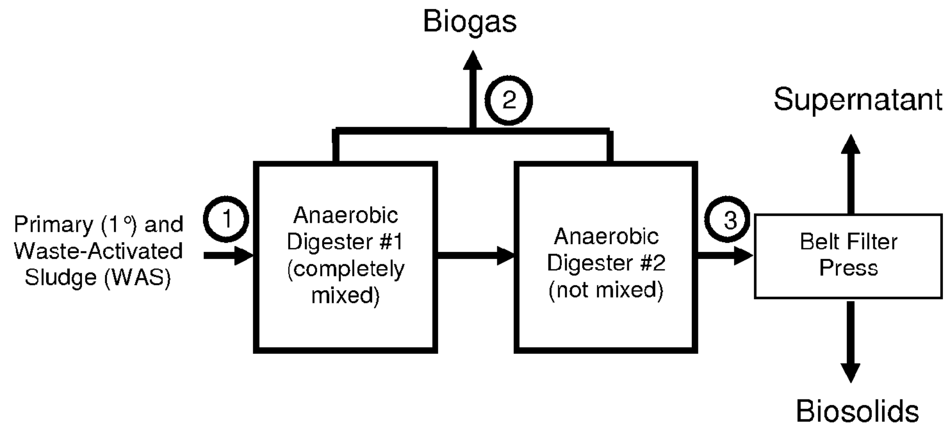
FIG. 1 is a flowchart depicting standard (prior-art) anaerobic digestion processes. At the top of the figure is shown a 2-Stage Anaerobic Digester (Conventional). At the bottom of the figure is shown a High-rate Anaerobic Digester.
Figure 1:
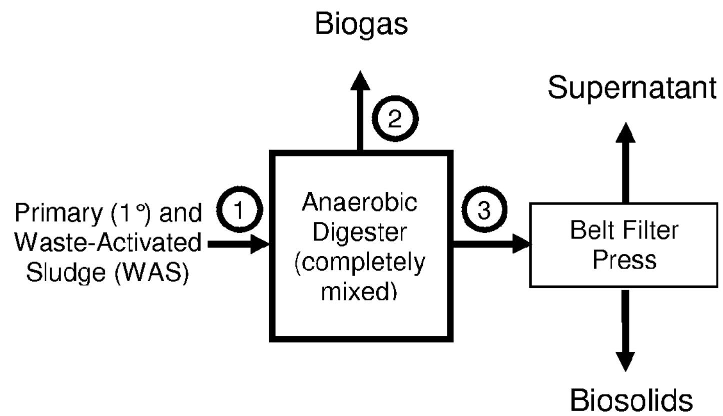

By way of background, a wastewater treatment system cleans wastewater before it is discharged into a receiving stream. Traditional anaerobic digestion is a stirred, low-solids process performed in a continuously-stirred tank reactor (CSTR). Both the conventional and high-rate processes use this design configuration. FIG. 1 presents a schematic block diagram of such conventional and high-rate processes that may be used by a municipality or the like. Typically, industrial or municipal primary and waste-activated sludge initially passes along a flow path into an anaerobic digester. In general, the micro-organisms consume the organic particulates suspended in the wastewater. In this way, the treatment microorganisms reduce contaminants present in the wastewater as well as the biological oxygen demand. Biogas, including methane, is one product of the digestion process. In a conventional, two-stage anaerobic digester the product to the first digestion is passed to a second anaerobic digester without additional mixing. Following the second anaerobic digestion, or, in the case of a high-rate anaerobic digester, a first anaerobic digestion, the digested product is passed to a belt filter press where the biosolids are separated from the supernatant. The stabilized, digested sludge can then proceed towards disposal.

Figure 2:
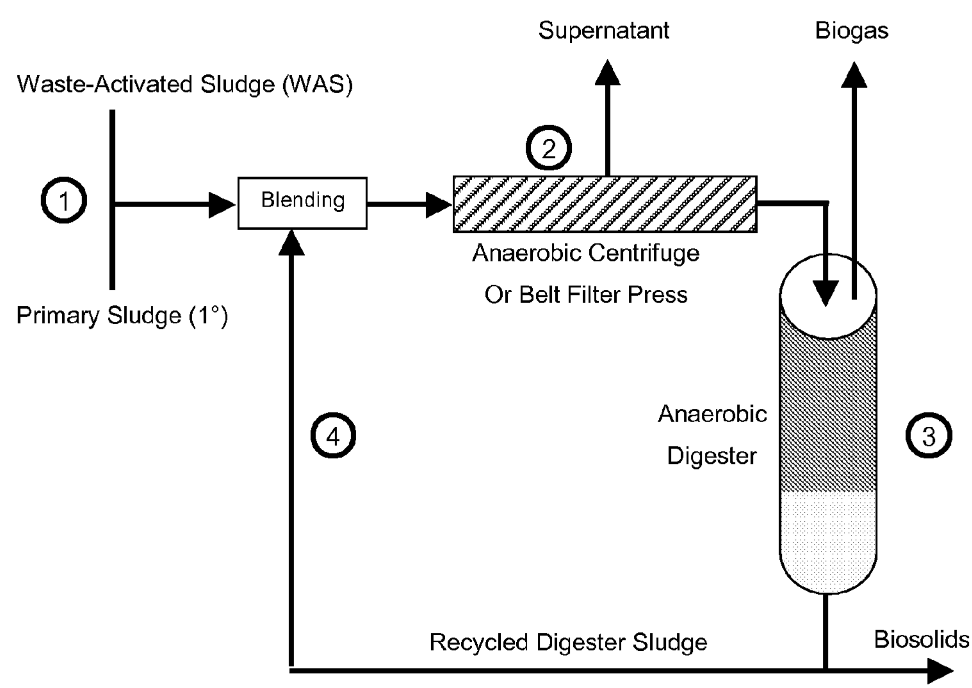
FIG. 2 is a flowchart depicting the anaerobic digestion process of the present invention.

The new anaerobic digestion process breaks the three tenets illustrated in FIG. 1. Referring to FIG. 2 there is presented a schematic block diagram exemplary of the invention. The new process converts a low-solids problem to a high-solids one. Whereas the conventional process deals with a total solids content of 1-4%, the new process thickens this solids content to 10-20%. This allows for a large reduction in reactor volume, thus generating large capital cost savings. Smaller reactor volume also means that different building materials than pre-stressed concrete can be used. The new process allows for standard sized plastic or metallic tanks. The conventional process requires stirring of the sludge, whereas the new process does not. Finally, the conventional process utilizes CSTRs, whereas the new process uses a plug-flow reactor (PFR) which is universally recognized as a more efficient reactor configuration. Eliminating excessive reactor size and stirring drastically reduces the equipment costs, and as a result, overall capital costs.

The invention will be further described by way of the following non-limiting examples.

EXAMPLE 1

Development and Characterization of the New Anaerobic Digestion Process

Process Steps for New Anaerobic Digestion Process:

1. Primary and waste activated sludge are blended with recycled anaerobic digester sludge.
2. The waste is thickened to increase the total solids content from 1-3% to 10-20%. Excess liquid (supernatant) from the centrifugation or belt filter press process is transferred to the head of the treatment plant for aerobic treatment. The thickened sludge is transferred into the anaerobic digester via an auger or similar system.
3. Thickened sludge is added to the anaerobic digester for a defined retention time. During this period, volatile solids are converted to biogas and biosolids. A portion of the biogas (methane and carbon dioxide) can be used to offset energy requirements for the digestion process. The digester temperature is maintained by a heating jacket and insulation. This is not possible in conventional or high-rate processes because of the size of the reactors. The digester is a plug flow reactor, and does not require stirring.
4. A portion of the digester waste stream is recycled as described in step one. The main purpose of this is to maintain the microorganism population in the digester. The remaining portion of the biosolids is removed for disposal or further processing.

Financial Benefits:

The equipment costs for conventional and high-rate digestion processes (serving 10,000 customers) are as follows:

| Equipment | Capacity | 2-Stage | High-rate |
|---|---|---|---|
| Anaerobic Digester #1 | 485,851 gal | $558,729 | — |
| Anaerobic Digester #2 | 485,851 gal | $558,729 | — |
| High-rate Anaerobic Digester | 364,388 gal | — | $470,152 |
| Gas Collection | | $120,000 | $60,000 |
| Total | | $1,237,000 | $530,152 |
| Capital Cost Factor | | 7× | 7× |
| Estimated Capital Costs | | $8,659,000 | $3,711,064 |

These costs are for systems serving 10,000 customers. Costs are in year 2000 dollars. Costs for belt filter presses, heating equipment, and pumps are not included because they are common to both systems. Gas collection equipment here are floating steel covers for the reactors. Costs are estimates based upon conversations with equipment vendors. However, the gas collection equipment is estimated to cost less for the new system, since costs are based upon surface area of the reactor. The PFR reactor for the new digestion method will not require a large floating cover or dome. The capital cost factor is based upon a conversation with a local environmental engineering consulting firm. Generally, capital costs for a project are six to seven times the total cost of equipment. The cost break down for the new system is as follows:

| Equipment | Capacity | New System |
|---|---|---|
| Anaerobic Digester | 42,026 gallons | $63,000 |
| Gas Collection | | $5000 |
| Total | | $68,000 |
| Capital Cost Factor | | 7× |
| Estimated Capital Costs | | $476,000 |

The digester costs are based upon a tank with dimensions of 32 feet tall by 15 feet diameter. It is sized for 15% solids with a hydraulic retention time of 15 days. Based upon these data, the equipment cost savings of the new process over the standard 2-stage system is 95%, and 87% versus the high-rate system.

| Capital Cost Savings | 2-Stage Process | High-rate Process |
|---|---|---|
| Percentage | 95% | 87% |
| Dollars | $8,183,000 | $3,235,000 |

It should be noted that the 15-day hydraulic retention time that our process is designed for is constrained by regulations for class A pathogen reduction (see EPA 40 CFR Part 503 for regulations for land application of biosolids). Our process retention time could be further reduced through lime additions to the treated biosolids to remove pathogens. Through this process, additional cost savings through reactor size reduction could be realized. It is also important to note that the dimensions for the reactor size listed here are for domestic/municipal sludge treatment only. Applications involving animal, crop, and other organic wastes may require smaller digesters, and will also likely have different disposal regulations.

Further Applications:

In addition to the digestion of municipal wastewater sludge, this technology lends itself to a variety of other waste digestion problems in industries such as: Swine manure (instead of covered lagoons), poultry waste, crop waste, paper waste, solid waste pre-landfill treatment, cattle waste, industrial waste, high-solid waste.

These waste streams would require further research and development to optimize the system operation; however the principle is sound and would likely only require minor adjustments. For instance, high-solids waste streams would require a dilution step to allow for homogeneous mixing of waste and anaerobic digester sludge. This would be accomplished by adding a small tank using process water prior to the thickening step. The smaller size and cost of the new system lends itself well to these applications, since conventional systems are cost and size prohibitive for the private user.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for treating sludge generated in a wastewater treatment system comprising the steps of:

blending sludge to be treated with recycled anaerobic digester sludge to form a blended sludge;

concentrating the blended sludge wherein the total solids content is increased to about 10% to about 20% and excess liquid is removed;

transferring the excess liquid for aerobic treatment;

digesting the concentrated sludge in a single vessel anaerobic digestion system wherein the digestion of the concentrated sludge is performed without substantially continuous stirring; and recycling a portion of the digester waste stream to provide as recycled anaerobic digester sludge input for the blending step.

2. The method according to claim 1 wherein the sludge to be treated is primary and waste activated sludge.

3. The method according to claim 1 wherein the sludge to be treated is selected from the group consisting of primary sludge and waste activated sludge.

4. The method according to claim 1 wherein the reactor of the anaerobic digestion system is a plug-flow reactor.

5. The method according to claim 1 wherein the temperature of the anaerobic digestion system is maintained by a heating jacket.

6. The method according to claim 1 wherein the anaerobic digestion system is insulated to maintain a substantially constant temperature.

7. The method according to claim 1 wherein the blended sludge is concentrated using a centrifuge.

8. The method according to claim 1 wherein the blended sludge is concentrated using a belt filter press.

9. The method according to claim 1 wherein the concentrated blended sludge is transferred to the anaerobic digestion system using an auger.

10. The method according to claim 1 wherein digesting the concentrated sludge in the anaerobic digester produces a biogas and a portion of the produced biogas is captured to offset the cost of the wastewater treatment system.

11. A method for treating sludge generated in a wastewater treatment system comprising the steps of:

blending sludge to be treated with recycled anaerobic digester sludge to form a blended sludge;

concentrating the blended sludge wherein the total solids content is increased to about 10% to about 20% and excess liquid is removed;

transferring the excess liquid for aerobic treatment;

digesting the concentrated sludge in a plug-flow reactor anaerobic digestion system; and recycling a portion of the digester waste stream to provide as recycled anaerobic digester sludge input for the blending step.

12. The method according to claim 11 wherein the anaerobic digestion system is maintained a substantially constant temperature.

13. The method according to claim 12 wherein the substantially constant temperature is maintained by heating the reactor.

14. The method according to claim 12 wherein the substantially constant temperature is maintained by insulating the reactor.

15. The method according to claim 11 wherein the digesting the concentrated sludge in an anaerobic digestion system is performed in the absence of substantially continuous stirring.

16. A method for treating sludge generated in a wastewater treatment system comprising the steps of:

providing primary and waste-activated sludge to be treated;

concentrating the sludge wherein the total solids content is increased to about 10% to about 20% and excess liquid is removed;

transferring the excess liquid for aerobic treatment; and digesting the concentrated sludge in a plug-flow reactor anaerobic digestion system.

17. The method according to claim 16 wherein the anaerobic digestion system is maintained a substantially constant temperature.

18. The method according to claim 17 wherein the substantially constant temperature is maintained by heating the reactor.

19. The method according to claim 17 wherein the substantially constant temperature is maintained by insulating the reactor.

20. The method according to claim 16 wherein the digesting the concentrated sludge in an anaerobic digestion system is performed in the absence of substantially continuous stirring.

* * * * *